United States Patent [19]

Callaway

[11] Patent Number: 5,480,651
[45] Date of Patent: Jan. 2, 1996

[54] COMPOSITION AND METHOD FOR TREATING NICOTINE CRAVING IN SMOKING CESSATION

[75] Inventor: Enoch Callaway, Tiburon, Calif.

[73] Assignee: Regents of the University of California, Oakland, Calif.

[21] Appl. No.: 213,111

[22] Filed: Mar. 15, 1994

Related U.S. Application Data

[63] Continuation-in-part of Ser. No. 121,606, Sep. 15, 1993, abandoned, which is a continuation-in-part of Ser. No. 851,914, Mar. 16, 1992, abandoned.

[51] Int. Cl.⁶ ...................................................... A61K 9/28
[52] U.S. Cl. ...................... 424/464; 424/451; 424/484; 514/304; 514/557; 514/161; 514/813
[58] Field of Search .................................. 424/464, 451, 424/484; 514/304, 557, 161, 813

[56] References Cited

U.S. PATENT DOCUMENTS

| | | | |
|---|---|---|---|
| 4,242,344 | 12/1980 | Lumma | 544/346 |
| 4,278,678 | 7/1981 | Madison et al. | 424/464 |
| 4,555,397 | 11/1985 | Bachynsky | 424/464 |
| 4,778,677 | 10/1988 | Ebbesen | 514/264 |
| 4,788,189 | 11/1988 | Glazer | 514/221 |
| 4,835,162 | 5/1989 | Abood | 514/305 |
| 4,940,585 | 7/1990 | Hapworth et al. | 424/464 |
| 4,952,586 | 8/1990 | Morris et al. | 514/304 |
| 4,966,916 | 10/1990 | Abood | 514/534 |
| 5,026,897 | 6/1991 | Chiang et al. | 560/58 |
| 5,035,897 | 7/1991 | Ayer et al. | 424/473 |
| 5,077,289 | 12/1991 | Glamkowski et al. | 514/211 |
| 5,102,666 | 4/1992 | Acharya | 424/487 |
| 5,153,193 | 10/1992 | Flanagan et al. | 514/228.8 |
| 5,171,750 | 12/1992 | Brossi et al. | 514/411 |
| 5,206,371 | 4/1993 | Powers et al. | 546/290 |
| 5,231,093 | 7/1993 | Flanagan et al. | 514/215 |
| 5,260,452 | 11/1993 | Glamkowski et al. | 548/486 |
| 5,264,442 | 11/1993 | Effland et al. | 514/339 |

OTHER PUBLICATIONS

Glassman et al., "Cigarette Craving, Smoking Withdrawal, and Clonidine", *Science*, 226, (1984) pp. 864–866.
Vidal et al., "Pharmacological Profile of Nicotinic Acetylcholine Receptors in The Rat Prefrontal Cortex," *Neuroscience*, vol. 29, No. 2, (1989), pp. 261–270.
Kaiser et al., "Cholinergic Agents", *Neurotransmissions*, vol. III, No. 2, (1987), pp. 1–5.
Reynolds (editor), *Martindale: The Extra Pharmacopoeia*, 29th edition, London: The Pharmaceutical Press, (1989), pp. 522, 534–536, 1328, 1333–1335, and 1594–1595.

Solana et al., "Comparing the Efficacy of Physostigmine Pretreatment in Combination with Scopolamine versus Artane Against Soman Challenge," Report USAMRICD–TR–88–19; Order No. AD–A201608 (1989).
Hrbek et al., "On the Acute Effects of Scopolamine (0.6 mg), Physostigmine (1.0 mg), and a Complex Combination of Both the Drugs on the Higher Nervous Activity in Man," *Acta Univ. Palacki. Olomuc., Fac. Med.*, 85, (1978) 281–327.
Harris et al., "Protection Against Diisopropylfluorophosphate Intoxication by Pyridostigmine and Physostigmine in Combination with Atropine and Mecamylamine," *Arch Pharmacol*, 327 (1984), pp. 64–69.
Stitcher et al., "Effects of Pyridostigmine and Cholirolytics on Cholisesterase and Acetylcholine in Soman Poisoned Rats," *Drug and Chemical Toxicology*, 1(4) (1978), pp. 355–362.
Cassone et al., "Effects of Combinations of Arecoline and Atropine on Mouse Motor Activity," *Prog. Neuro–Psycholpharmacol. & Biol. Psychiat.*, 14 (1990), pp. 83–90.
Eriksen et al., "Effects on Muscarinic Receptors of Various Agents in Reversal of NeuropMuscular Blockade . . . , " *Chemical Abstracts*, vol. 89, No. 23, Item 191258k.
Rose and Levin, "Concurrent Agonist–Antagonist Administration for the Analysis and Treatment of Drug Dependence," *Pharmacology Biochemistry and Behavior*, 41, pp. 219–226, 1991.
Iijima et al., "Phenserine: A Physostigmine Derivative that is a Long–Acting Inhibitor of Cholinesterase and Demonstrates a Wide Dose Range for Attenuating a Scopolamine–Induced Learning Impairment of Rats in a 14–unit T–Maze," *Psychopharmacology*, 112, pp. 415–420, 1993.
Smith et al., "Methylatropine Blocks the Central Effects of Cholinergic Antagonists," *Behavioural Pharmacology*, 5, pp. 167–175, 1994.
Chem. Abst., vol. 116, No. 1, Item 656g.

*Primary Examiner*—Raj Bawa
*Attorney, Agent, or Firm*—Majestic, Parsons, Siebert & Hsue

[57] ABSTRACT

A method for relieving craving in a nicotine-habituated patient and a composition for treating the patient is provided. The composition administered has a non-specific acetylcholine agonist and a muscarinic agonist. A particularly preferred composition for relieving craving takes the form of a tablet where the first component is a water soluble physostigmine and the second component is a water soluble scopolamine. Patients treated have reported a slight increase in alertness and a diminished craving for nicotine.

8 Claims, No Drawings

COMPOSITION AND METHOD FOR TREATING NICOTINE CRAVING IN SMOKING CESSATION

This invention was made with government support under The Veterans Administration and Grant No. MH-22149, awarded by the National Institutes of Health. The government has certain rights in this invention. This is a continuation-in-part of Ser. No. 08/121,606, filed Sep. 15, 1993, now abandoned, which is a continuation-in-part of Ser. No. 07/851,914, filed Mar. 16, 1992, now abandoned.

FIELD OF THE INVENTION

The present invention generally relates to treating smoking withdrawal symptoms, and more particularly to a composition useful in relieving craving in a nicotine-habituated patient abstaining from or reducing nicotine intake.

BACKGROUND OF THE INVENTION

The statistical risk of dying from lung cancer in the United States has doubled in the past thirty years for male cigarette smokers and has quadrupled for female cigarette smokers. Lung cancer has now displaced cardiovascular disease as the single most important cause of excess mortality among smokers. Yet, about 50 million Americans continue to smoke.

The benefits for smoking cessation are many, and are summarized in a publication entitled "The Health Benefits of Smoking Cessation: A Report of the Surgeon General, 1990", available from the Office on Smoking and Health, Center for Disease Control, Rockville, Md. Among the benefits summarized are that within twenty-four hours the chance of a heart attack decreases, within about two weeks to three months lung function increases up to thirty percent, and in one year the excess risk of coronary heart disease becomes half that of a smoker.

Glassman et al. in an article entitled, "Cigarette Craving, Smoking Withdrawal, and Clonidine," Science, 226, pp. 864–866 (November 1984), describes the craving developed for the tension-reducing drug, nicotine, in the absence of the drug and attributes the craving to the habituated user's experience of a rebound dysphoria. The habituated user thus seeks the drug to eliminate that dysphoria in order to treat, or relieve, craving when the person is attempting to abstain from or is reducing nicotine intake.

Smoking cessation programs often address both the physiological (biochemical) factor and the psychological factor. Recently, "nicotine-releasing patches" have been highly advertised, and are presumably useful by maintaining a nicotine-habituated patient on nicotine while addressing the psychological factor. Methods that maintain a patient on nicotine do not provide a long term solution to the problem. For example, there are now a number of patients addicted to nicotine containing gum, some of whom are seeking treatment for their new or substitute addiction.

Glassman et al., Science, 226, pp. 864–866 (1984) describe use of clonidine or alprazolam in diminishing withdrawal symptoms when fifteen heavy smokers abstained from cigarettes. The authors suggest that noradrenergic activity may be a common feature in the pathophysiology of withdrawal and that a special relationship may exist between central noradrenergic activity and craving. The authors noted that previous studies of smoking withdrawal syndrome had shown that craving is the most consistently observed withdrawal symptom.

U.S. Pat. No. 4,788,189, issued Nov. 29, 1988, inventor Glazer, suggests administering clonidine hydrochloride with an imipramine derivative in a method to treat smoking withdrawal symptoms. Clonidine is clinically used as an antihypertensive while imipramine is an antidepressant. However, recent studies suggest that the side effects of clonidine (largely anticholinergic) make it unacceptable.

U.S. Pat. No. 4,555,397, issued Nov. 26, 1985, inventor Bachynsky, describes subcutaneously injecting a patient during an initial office visit with a composition containing atropine, scopolamine, and chlorpromazine. Following the initial office visit and treatment, the patient is placed upon dosages of predominately centrally acting anticholinergic drugs (such as scopolamine by patch administration).

Atropine and scopolamine are alkaloids that block the action of acetylcholine at muscarinic receptors to produce antispasmodic, antisecretory, and antiparkinsonism actions. Scopolamine (sometimes also called "hyoscine") is a powerful suppressant of salivation (as is atropine), and is effective in the prevention and control of motion sickness.

Physostigmine (sometimes called "eserine") is an inhibitor of acetylcholine metabolism (by inhibiting the enzyme acetylcholinesterase) and is an antagonist of scopolamine. Since the action of acetylcholine is terminated by its rapid hydrolysis into choline and acetic acid, acetylcholinesterase inhibitors prolong or mimic the action of the neurotransmitter, acetylcholine.

Acetylcholine is released into synapses where it behaves as a neurotransmitter that associates with macromolecular receptors. The association of acetylcholine with its receptors initiates a physiological response, probably by opening membrane ion channels. The acetylcholine receptors appear to be of two general subtypes. One subtype appears to have nicotine as an agonist (that is, the nicotine molecule appears to fit into the one subtype of acetylcholine receptor). For example, the nicotinic effect of acetylcholine can be revealed when its degradation by acetylcholinerase is inhibited, as is discussed by Vidal and Changeux, Neuroscience, 29 (2), pp. 261–270 (1989). The other general subtype of acetylcholine receptors is muscarinic. Muscarine is an alkaloid that mimics the action of acetylcholine on muscarinic receptors.

Activation of cholinergic receptors results in bradycardia, increased secretion (e.g. salivary and sweat), gastrointestinal contractions, and other symptoms. Hypotensive, cardiac inhibitory effects caused by low doses of acetylcholine are similar to those produced by muscarine and appear to be mediated via muscarinic acetylcholinase receptors at postganglionic parasympathetic terminals, whereas effects at autonomic ganglion and skeletal neuromuscular junctions result from nicotinic acetylcholine receptors.

SUMMARY OF THE INVENTION

In one aspect of the present invention, a method for relieving craving in a nicotine-habituated person who is abstaining from or reducing nicotine intake is provided by administering an admixture of first and second components. The first component is a non-specific acetylcholine agonist, preferably having at least one determinable muscarinic effect and one determinable nicotinic effect, and the second component is a muscarinic antagonist having a determinable antimuscarinic effect.

Administration of a balanced admixture of the first and second components relieves craving, yet surprisingly results in substantially no identifiable muscarinic or antimuscarinic changes. Instead, practice of the invention appears merely to increase alertness without tenseness, and yet to reduce craving in persons who are abstaining from nicotine intake.

A particularly preferred composition of the invention takes the form of a tablet suitable for oral administration wherein the first component is a water soluble physostigmine and the second component is a water soluble scopolamine. The combination of the first and second components is surprising because the two classes of drugs (non-specific acetylcholine agonist and muscarinic antagonist, respectively) have been viewed as mutual antagonists with antimuscarinics being conventional antidotes for anticholinerase poisoning. Further, the inventive compositions have been shown to lead to a reduced desire for nicotine, which is greater than when persons were administered a comparative composition with only physostigmine. This shows that scopolamine does not merely alleviate side effects of physostigmine, but rather that the two components are acting together in reducing desire for nicotine in nicotine-habituated persons.

DETAILED DESCRIPTION OF THE PREFERRED EMBODIMENTS

Practice of the inventive method comprises administrating an admixture that must include two essential components. The first component is a non-specific acetylcholine agonist. The first component preferably has at least one determinable muscarinic effect and one determinable nicotinic effect were it administered by itself. By "non-specific" is meant that the actions of the first component are not limited to one class or type of acetylcholine receptors, but rather that the first component acts on both the muscarinic receptors and the nicotinic receptors.

By a "determinable muscarinic effect" is meant that pharmacologically effective dosages will produce one or more of the typical muscarinic effects. (e.g. sweating, salivation, increased gastrointestinal motility, and heightened alertness). Drugs with antimuscarinic action have been suggested as anti-smoking agents, but their side effects (dry mouth, reduced alertness) make them unacceptable to most potential users. As will be further discussed hereinafter, the inventive combination of first and second components avoids muscarinic side effects (e.g. nausea) and also antimuscarinic side effects.

By a "determinable nicotinic effect" is meant typical activation of nicotinic receptors when a physiologically effective dose is administered, such as one or more of increased skeletal or muscle excitability, opening of sodium channels in nicotine-sensitive receptors, as can be determined by patch-clamp techniques, and so forth.

The second component is a muscarinic antagonist that preferably has at least one determinable antimuscarinic effect were it administered by itself. By a "determinable antimuscarinic effect" is meant dry mouth, dry skin, impaired attention or alertness, and decreased gastrointestinal motility.

Inventive admixtures of the first and second components are in a balanced weight ratio of first and second components sufficient substantially to eliminate the determinable muscarinic and antimuscarinic effects (with the exception of some typical increased alertness), yet to be in an amount effective substantially to relieve nicotine craving for a duration of time. The duration in which craving is relieved depends upon several factors, such as the duration of action for the particular first and second components chosen, the particular patient (degree of habituation, weight, etc.), but preferably is on an order of several hours. One inventive combination is physostigmine and scopolamine. Although physostigmine has an apparent duration of activity that seems sufficiently equivalent to scopolamine, various analogues of physostigmine, other types of anticholinergics and various sustained release preparations of the above, particularly those having longer duration of activity, are believed useful and even better matched to the duration of scopolamine.

The balance of first and second components for the admixture will normally be readily determined empirically by the physician or health care professional treating the nicotine-habituated patient, in establishing the proper doses. Treatment begins with established, pharmaceutically effective doses of each component by itself, then by establishing through observation and discussion with the patient whether the balance has been established that is sufficient substantially to eliminate the determinable muscarinic and antimuscarinic effects yet while being in an amount effective substantially to relieve nicotine craving for some measurable period of time.

Each of the first and second components must be able to pass the blood-brain barrier (usually due to a lipophilic nature) so as to have central nervous system effects. As will be more fully described hereinafter, a particularly preferred first component is a water soluble physostigmine and a particularly preferred second component is a water soluble scopolamine, with the inventive admixture having the first and second components most preferably in about a 5:1 weight ratio such an admixture relieves craving for about four hours.

Among the non-specific acetylcholine agonists suitable as the first component are physostigmine, (including analogues and derivatives) methacholine, edrophonium, quaternary tetraalkylammonium salts, 9-amino-1,2,3,4-tetrahydracridine (also known as "tacrine"), diisopropyl fluorophosphate, paraoxon, and soman. The latter three are quite potent and long-acting. These non-specific acetylcholine agonists include both reversible and irreversible inhibitors of acetylcholinesterase and also direct agonists such as arecoline. Some other illustrative non-specific acetylcholine agonists believed useful as the first component are 4-aminopyridine, choline alfoscerate, eptastigmine, eseridine salicylate, galantamine hydrobromide, linopirine, RS-86, and suronacrine maleate.

Suitable first and second components are preferably in a water soluble form, such as being present as pharmaceutically acceptable salts, which is meant to include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

Physostigmine is generally regarded as an irreversible acetylcholinesterase inhibitor because it forms a covalent bond with the catalytic site of the enzyme. Physostigmine is preferred as the first component due to an apparent duration of activity that seems sufficiently equivalent to the preferred second component (although classical pharmacokinetics suggest physostigmine has a shorter half-life than scopolamine), and due to its orally active forms. In addition, there is evidence that physostigmine may, in addition to its non-specific effect, act as a direct nicotinic agonist via a novel receptor site, hence having additional desirable nicotinic action, although pharmacokinetics of this action in humans has not been studied.

A number of physostigmine analogues are also known and are useful as the first component, particularly when having a duration of action longer than physostigmine (up to about an eight hour duration when using scopolamine as the second component). For example, U.S. Pat. No. 5,171,750, issued Dec. 15, 1992, inventors Brossi et al., incorporated herein by reference, discloses a number of substituted phenylcarbamate or napththylcarbamate tricyclic compounds structurally related to physostigmine; U.S. Pat. No. 5,077,289, issued Dec. 31, 1991, inventors Glamkowski et al., incorporated herein by reference, discloses derivatives related to physostigmine; U.S. Pat. No. 5,153,193, issued Oct. 6, 1992, inventors Flanagan and Martin, incorporated herein by reference, discloses more analogues of physostigmine; and U.S. Pat. No. 5,260,452, issued Nov. 9, 1993, inventors Glamkowski and Kurys, incorporated herein by reference, discloses 4- and 6-carbamates related to physostigmine.

Particularly preferred forms of physostigmine (including analogues) are water soluble derivatives, and include physostigmine salicylate and physostigmine sulfate. Physostigmine crosses the blood-brain barrier and can be administered subcutaneously, intramuscularly, by slow intravenous injection, and orally (when in the water soluble salicylate or sulfate forms).

Muscarinic antagonists suitable as the second component include scopolamine, atropine, benactyzine, oxybutynin, quinuclidinyl benzilate, 3-quinuclidinyl-xanthene-9-carboxylate, and quinuclidinyl atrolactate. However, not preferred are muscarinic antagonists that have limited or no central antimuscarinic effects, such as methoctramine. The water soluble scopolamine derivatives are particularly preferred, such as scopolamine butylbromide, scopolamine hydrobromide, and scopolamine methobromide. The quaternary derivatives (butylbromide, methobromide, and methonitrate) do not readily cross the blood-brain barrier. Scopolamine hydrobromide is a particularly preferred water soluble scopolamine for use as the second component.

Compositions for use in the inventive method for relieving craving preferably are formed as tablets or capsules suitable for oral administration and have the first and second components admixed therein. The quantities of first and second components so admixed are wherein a dose comprised by one or more tablets, is effective substantially to relieve nicotine craving for a duration of time, preferably several hours, most preferably about three hours or more.

Where, for example, the first and second components are water soluble physostigmine and water soluble scopolamine, then each tablet preferably has the components in about a 5:1 weight ratio with the soluble physostigmine preferably being in a range of 0.5–3 mg and the scopolamine preferably being in a range of 0.1–6 mg, and each tablet delivers a dose of about 0.6 mg. Tablets of the invention optionally include one or more pharmacologically suitable component or components such as buffering agent, preservative (e.g. antioxidants), excipients and/or tabletting agents, flavoring agents, and the like. Suitable such components are well-known to the tabletting art.

Composition embodiments of the invention were formulated and administered to patients by a treating physician as will now be described for purposes of illustrating the invention.

The persons who participated in the study had consented to be research subjects, and the Committee on Human Research, Office of Research Affairs of the University of California, San Francisco Institutional Review Board had reviewed and approved the application to involve humans as research subjects in the study.

Patients (subjects) were chosen who were unable to stop smoking and were able to verbally report their feelings of craving. Once every four or more days the patient met with a treating physician at an agreed-upon time when the patient expected to experience craving for nicotine to a degree that would ordinarily cause the patient to smoke a cigarette. For example, the subject will have refrained from using nicotine just before his or her appointment so that the subject was expected to be experiencing strong, but tolerable, craving within an hour after coming to the laboratory. The patient's heart rate, blood pressure, and temperature were recorded and a questionnaire about the patient's moods was filled out and the degree of craving was rated on a simple scale. A composition of the invention was then administered and over the following two hours the patient rated his or her craving on the scale at fifteen minute intervals and, with the help of the treating physician, made a record of various reactions (happy, anxious, tense, and so forth). At the first few interviews balanced amounts of physostigmine and scopolamine were established for each patient (where substantially no sweating, increased GI activity, and bowel cramping, one hand, and no dry mouth, trouble concentrating, and a "spacey" feeling, on the other hand, were experienced), but where craving for nicotine was diminished.

In broader use of the inventive composition, persons attempting to abstain from nicotine intake will probably self-medicate. A recommended dose for self-medication is likely a maximum of about six capsules per day (each preferably with 0.1 mg of water soluble scopolamine hydrobromide and 0.5 mg water soluble physostigmine salicylate for one preferred embodiment) at the rate of about one capsule per hour to one per three hours.

EXAMPLE 1

Smokers (some of whom were nicorette-users) attempting to abstain from nicotine intake were initially administered small doses of scopolamine (HBr, 0.3 mg) and physostigmine ($SO_4$, 0.3 mg) tabletted with 0.5 g ascorbic acid as a stabilizing (antioxidant) agent. Pulse, blood pressure (systolic/diastolic) and orally taken temperature were recorded. Each patient rated him or herself on a sliding scale between happy/sad, extra alert/sleepy, clear or sharp/dull, anxious/calm, tense/relaxed, energetic/lazy, and on the degree of craving (worst ever/thought of nicotine is repulsive).

Table 1 summarizes data from six persons participating in the study.

TABLE 1

| Subject | Age | Nicotine Consumption | Dose (mg) | Pulse Drop | Pulse Time Occur. (min) | Craving Relief | Crav. Time Occur. (min) | Duration (min) |
|---|---|---|---|---|---|---|---|---|
| 1 | 56 | 20 Cig. & | 0.3 | 15 | 75 | 50% | N/A | N/A |
|   |    | Nic. gum  | 0.6 | 35 | 130 | 75% | 70 | 120 |
| 2 | 55 | 20 Cig. | 0.3 | 12 | 90 | 50% | N/A | N/A |
|   |    |         | 0.6 | 07 | 90 | 65% | 75 | 45 |
|   |    |         | 0.9 | 17 | 75 | 60% | 30 | 120 |
| 3 | 37 | 20 | 0.3 | 16 | 60 | 60% | 75 | 120 |
|   |    |    | 0.6 | 20 | 105 | 70% | 75 | 75 |
| 4 | 41 | 20 | 0.3 | 20 | 120 | 75% | 60 | 120 |
|   |    |    | 0.6 | 14 | 45 | 75% | 45 | 135 |
| 5 | 40 | Nic. gum | 0.6 | 12 | 50 | 50% | N/A | N/A |
| 6 | 38 | 20 Cig. | 0.3 | 27 | 105 | 60% | 105 | 60 |
|   |    |         | 0.6 | 11 | 60 | 80% | 30 | 150 |

Subjects were given the selected dose and then were monitored and tested with a variety of scales and for vital signs (including temperature). Of the vital signs, only pulse rate changed. There were no significant reports of autonomic side effects. The craving scale was from "0" (meaning "worst craving for a cigarette ever") to "100" (meaning "the thought of smoking is disgusting"). A value of "50" was generally interpreted as the craving felt about one-half hour after a usual cigarette had been smoked.

With specific reference to the data for Subject 1 for illustration, this subject was smoking an average of 20 cigarettes a day plus was using nicotine containing gum. The patient was initially treated with a dose containing 0.3 mg of each scopolamine and physostigmine. Immediately after receiving this dose, the subject's pulse rate began to be monitored. The "pulse drop" category was the maximum drop in beats per minute that occurred. The "pulse time occur" category means the number of minutes following administration of the dose when the maximum pulse drop occurred. In "craving relief" the 50% craving relief was not considered evidence of reduced craving. Only ratings of 60% or more were considered as evidence of reduced craving. The "craving time occur" was the time that had elapsed from taking the dose when the craving relief (if present) was rated, whereas the "duration" was the additional amount of time that the patient spent in the laboratory and felt there had been craving relief. For example, when Subject 1 (who was still experiencing craving with 0.3 mg of each component) subsequently received an increased dose of 0.6 mg of each component, then the subject did experience craving relief (rated as 75%), which was experienced 70 minutes after receiving the dose, and which craving relief lasted at least two hours after the initial 70 minute period (while the patient was yet in the laboratory). Patients did report to the investigating physician that they had various degrees of continued craving relief after leaving the laboratory.

As seen by Table 1, at doses of 0.6 mg (of each drug), all subjects but one experienced a relief of craving for two or more hours. The onset of reduced craving and pulse rate minimum usually coincided.

Thus, relief from craving is obtained for at least some patients when as little as 0.3 mg of each drug in the combination was administered with the craving relief lasting from three to six hours. The only side effect observed has been bradycardia at the lowest dose, which is less marked at the higher doses, but this has not been troublesome. A definite subjective effect has been noted. Neither dry mouth nor increased gastrointestinal activity has been noted. Pupil size has not shown a measurable change in the either direction.

EXAMPLE 2

A second study was designed to determine whether the inventive composition reduces the desire for nicotine. Healthy volunteer smokers, age 18–55 years (mean 30.3 years), were recruited for the study. To increase the likelihood of nicotine dependence and withdrawal symptoms, subjects were required to habitually smoke at least one pack per day of a cigarette brand delivering $\geq 0.5$ mg nicotine by FTC analysis. (The mean was 26 cigarettes per day.) For subject safety, a history, physical, serum chemistries, complete blood count, and resting electrocardiogram was performed prior to study enrollment. Subjects with significant medical or psychiatric disorders were excluded to decrease the chances of untoward effects. The subjects had a mean of 1.3 quit attempts.

After screening history and physical, subjects were instructed to come to the laboratory for each study day. Subjects were told to refrain from smoking as best they could on the study days. (It was emphasized that these study days were not quit attempts.)

Subjects on study days participated in a nicotine preference test. The nicotine preference test allows the subject to regulate the nicotine content in smoke when he/she takes a puff from a cigarette during the test. The nicotine content is regulated by using an apparatus which changes the proportion of smoke from a high nicotine and low nicotine cigarette by the use of a dial operated by the subject. There are three dial settings: 30% high nicotine; 50% high nicotine; and 70% high nicotine. The subject self-regulates the nicotine content for puffs four and five (which are then averaged in compiling the data), but puffs one, two, and three give the subject the following proportion of smoke from the high nicotine cigarette: puff one at 50% high nicotine; puff two at 70% high nicotine; and puff three at 30% high nicotine.

At the beginning of the study day, subjects received one of three test compositions. Test Composition 1 was physostigmine salicylate (0.5 mg) by itself. Test Composition 2 was placebo. Test Composition 3 was an inventive embodiment of physostigmine salicylate (0.5 mg) plus scopolamine hydrobromide (0.1 mg). At two intervals after taking one of the three test compositions, the volunteers participated in the nicotine preference test. The first interval was one hour and thirty minutes after receiving a test composition, while the second interval was two hours and fifteen minutes after receiving a test composition.

Subjects who were administered the placebo had a 67.2% high nicotine cigarette preference. Subjects who were administered the test composition with only physostigmine had a 54.8% high nicotine cigarette preference. However, subjects who had been administered the inventive embodiment composition had a significantly reduced 47.6% high nicotine cigarette preference. This illustrates that treatment with an inventive composition reduces nicotine preference and thus the inventive compositions lead to a reduced desire for nicotine. Further, the data shows that scopolamine in the composition plays a direct role in resulting in a reduced desire for nicotine, rather than merely alleviating the side effects of physostigmine.

It is to be understood that while the invention has been described above in conjunction with preferred specific embodiments, the description and examples are intended to illustrate and not limit the scope of the invention, which is defined by the scope of the appended claims.

It is claimed:

1. A method for relieving craving in a nicotine-habituated person abstaining from or reducing nicotine intake by administering an admixture consisting essentially of a first component that either prolongs or mimics the effect of acetylcholine and a second component being a muscarinic antagonist wherein the first component is selected from the group consisting of physostigmine, physostigmine analogues, tacrine, methacholine, edrophonium, and water soluble derivatives thereof, and wherein the second component is selected from the group consisting of scopolamine, atropine, and water soluble derivatives thereof, with the first and second components being in a weight ratio ranging from about 1:1 to 10:1.

2. The method as in claim 1 wherein the admixture optionally includes a pharmacologically suitable component selected from the group consisting of a solvent, a buffering agent, a perservative, an excipient, a flavoring agent, a tabletting agent, and mixtures thereof.

3. The method as in claim 1 wherein the administration is an oral dose.

4. A composition for treating a nicotine-habituated person abstaining from or reducing nicotine intake consisting essentially of:

first and second components in tabletted form suitable for oral administration, the first component either prolonging or mimicking the effect of acetylcholine and the second component being a muscarinic antagonist, a dose of one or more tablets being effective to relieve nicotine craving for a period of time, wherein the first component is physostigmine salicylate in an amount between about 0.5 to about 3 mg, and the second component is a scopolamine salt in an amount between about 0.1 to about 0.6 mg.

5. The composition as in claim 4 wherein the first component is a water soluble physostigmine salicylate or physostigmine salicylate analogue.

6. The composition as in claim 4 wherein the composition optionally includes a pharmacologically suitable component selected from the group consisting of a buffering agent, a preservative, an excipient, a flavoring agent, a tabletting agent, and mixtures thereof.

7. The method as in claim 1 wherein the first component is a water soluble derivative of physostigmine or a physostigmine analogue and the second component is a water soluble derivative of scopolamine.

8. The composition as in claim 4 or 6 wherein the second component is scopolamine hydrobromide.

* * * * *